(12) United States Patent
Williams et al.

(10) Patent No.: US 9,060,759 B2
(45) Date of Patent: Jun. 23, 2015

(54) ADJUSTABLE-THROW BIOPSY NEEDLE

(75) Inventors: Rachel Williams, Rockford, IL (US);
Raymond Humphrey, Bloomington, IN (US); Ruth Osbrink, North Riverside, IL (US); Tim Fish, Gosport, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 317 days.

(21) Appl. No.: 13/433,801

(22) Filed: Mar. 29, 2012

(65) Prior Publication Data

US 2012/0253230 A1 Oct. 4, 2012

Related U.S. Application Data

(60) Provisional application No. 61/469,850, filed on Mar. 31, 2011.

(51) Int. Cl.
*A61B 10/00* (2006.01)
*A61B 10/02* (2006.01)

(52) U.S. Cl.
CPC ..... *A61B 10/0275* (2013.01); *A61B 2010/0208* (2013.01)

(58) Field of Classification Search
CPC ........... A61B 10/02; A61B 2010/0208; A61B 10/0233; A61B 10/0266; A61B 10/0275
USPC ................... 600/562–568; 606/167, 170, 171
See application file for complete search history.

(56) References Cited

U.S. PATENT DOCUMENTS

| | | |
|---|---|---|
| 3,995,619 A | 12/1976 | Glatzer |
| 4,600,014 A | 7/1986 | Beraha |
| 5,156,160 A | 10/1992 | Bennett |
| 5,172,702 A | 12/1992 | Leigh et al. |
| 5,195,533 A | 3/1993 | Chin et al. |
| 5,313,958 A | 5/1994 | Bauer |
| 5,916,175 A | 6/1999 | Bauer |
| 5,989,196 A | 11/1999 | Chu et al. |
| 6,203,925 B1 | 3/2001 | Attard et al. |
| 6,749,576 B2 | 6/2004 | Bauer |
| 7,481,775 B2 | 1/2009 | Weikel, Jr. et al. |
| 7,517,322 B2 | 4/2009 | Weikel et al. |
| 7,717,861 B2 | 5/2010 | Weikel et al. |
| 7,730,608 B2 | 6/2010 | Kvalheim |
| 7,766,843 B2 | 8/2010 | Voegele |
| 7,846,109 B2 | 12/2010 | Parihar et al. |
| 7,862,518 B2 | 1/2011 | Parihar |
| 8,096,773 B2 | 1/2012 | Chang |
| 2004/0153003 A1 | 8/2004 | Cicenas et al. |
| 2004/0167434 A1 | 8/2004 | Fisher |
| 2006/0200041 A1 | 9/2006 | Weikel et al. |
| 2006/0200042 A1 | 9/2006 | Weikel et al. |
| 2007/0208272 A1 | 9/2007 | Voegele |
| 2010/0312141 A1* | 12/2010 | Keast et al. ................... 600/567 |
| 2011/0190660 A1* | 8/2011 | Levy ............................ 600/566 |

* cited by examiner

*Primary Examiner* — Max Hindenburg
*Assistant Examiner* — Jonathan M Foreman
(74) *Attorney, Agent, or Firm* — Woodard, Emhardt, Moriarty, McNett & Henry LLP

(57) ABSTRACT

Among other things, there is disclosed a biopsy needle system in which the needle is capable of obtaining more than one length of sample. Generally, the needle includes an inner stylet, an outer cannula, and a handle connected to the stylet and cannula. The stylet has a notch that is extendable from the cannula to accommodate a tissue sample. An insert member is provided for attachment to the handle to make the amount of exposed notch smaller. Consequently, when the insert member is not attached to the handle, the needle can obtain a larger sample of tissue, and when the insert member is attached to the handle, the needle can obtain a smaller sample of tissue.

19 Claims, 4 Drawing Sheets

ADJUSTABLE-THROW BIOPSY NEEDLE

REFERENCE TO RELATED APPLICATIONS

This application claims the benefit of U.S. Provisional Patent Application No. 61/469,850, filed Mar. 31, 2011, which is hereby incorporated by reference.

The present disclosure concerns devices such as biopsy needles for obtaining a sample of human or animal tissue for testing or study. In particular, it concerns tissue-obtaining devices that allow a user to choose from among two or more sizes of sample, and methods for using such devices.

BACKGROUND

A variety of biopsy needles and similar devices for obtaining a tissue sample from a patient are known. Commonly, such devices include a thin needle or stylet that can be inserted into the skin of the patient near the location of tissue to be sampled, such as suspected malignancies or other tissue of interest. Once the distal end or other cutting portion of the needle or stylet is within the tissue of interest, a portion of the tissue is excised and captured. The needle or stylet is withdrawn with the tissue sample, which can be retrieved from the device and studied.

Such products have proven quite effective in obtaining tissue in a minimally-invasive manner and with minimal discomfort to the patient. Their lightweight nature, combined with their ease of operation and reusability, make them excellent for sampling tissue that may present or indicate a health problem to the patient.

Biopsy needles are generally designed to obtain samples of a fixed length, and in many cases that setting is either for a length of sample of 10 mm or 20 mm. Consequently, a range of needles for both sample-lengths (and perhaps others) must be on hand in the biopsy facility so that the physician or other clinician will be able to obtain the sample length appropriate to the given situation. Further, there are often cases where the clinician is uncertain as to which sample size is appropriate for the given patient or the given situation. For example, having estimated that a 10 mm length of sample will do, a clinician might decide after a few such 10 mm samples that he or she needs to obtain more tissue to retrieve an adequate, testable sample. He or she would then have to dispose of the used 10-mm-sample biopsy needle and replace it with a new 20-mm-sample needle. This is inconvenient, and introduces additional cost for supplies for the overall procedure in addition to potential additional discomfort to that patient.

Thus, if the tissue of interest is easily findable and of a size easily determined by the clinician, then he or she can choose a product that will provide the amount of tissue suggested by the patient's situation. However, in other cases there may be less certainty, meaning that the clinician may make an ultimately incorrect estimate of how much tissue to obtain, and therefore may have to use multiple biopsy devices to obtain samples of differing lengths or amounts. Further, hospitals, clinics and other health service providers must stock multiple versions of biopsy needles to be sure of having a product suited to particular needs, with the associated accounting, capital outlay and other administrative tasks associated with multiple products. There remains a need for tissue sampling devices capable of obtaining varying amounts of tissue depending on a particular situation while maintaining the ease of use of the device.

SUMMARY

Among other things, there is disclosed a biopsy needle having an inner stylet member with a distal end and defining a longitudinal notch of at least a default length, an outer cannula member having a sharpened distal end and a lumen within which the stylet member is slidable, and a handle connected to each of the stylet and cannula and operable to move the stylet and cannula with respect to each other. An insert member is provided separate from and attachable to the handle member. When the insert member is not attached to the handle, the needle has a first sampling size, and when the insert member is attached to the handle, the needle has a second sampling size less than the first sampling size. In certain embodiments, the first sampling size is equal to or less than the default length of the notch. The insert member can include a central shaft, and when the insert member is attached to the handle, its central shaft impedes distal movement of the stylet relative to the cannula. Embodiments of the central shaft may have at least one longitudinally-oriented camming surface, and the insert member may also include a pair of arms laterally offset from the central shaft, with each arm connects to the handle at a respective one of the handle's holes or finger holds. Where the handle includes a central longitudinal channel, the shaft can occupy a portion of the channel. The stylet may be adapted to extend from the cannula, and the maximum amount of the stylet that can extend from the cannula is greater when the insert member is not attached to the handle than when the insert member is attached to the handle. In some embodiments, the handle includes a carriage connected to said cannula member and having a longitudinal groove. When the insert member is attached to the handle, at least a portion of the insert member is linearly aligned with the groove. A system or kit can include a plurality of such insert members, each such insert member having a respective shaft, and each such shaft has a different length.

In other embodiments, a biopsy system is disclosed that includes a biopsy needle having a handle, an outer cannula, and an inner stylet having a longitudinal notch. The stylet and cannula are movable with respect to each other between a first relative position in which the notch is within the cannula and a second relative position in which at least a portion of the notch is exposed from the cannula. At least one insert member is provided that has a central shaft and is adapted to be attached to the handle so that the shaft is along the direction of travel of one or both of the stylet and cannula. The needle has a default condition in which the amount of the notch exposable from said cannula has a first length, and when an insert member is attached to the handle, the amount of the notch exposable from the cannula has a second length less than the first length.

Embodiments of such a system may have at least two such insert members, with the shaft of a first insert member having a first length, and the shaft of a second insert member having a second length different from the first length. The amount of the notch exposable from the cannula when the first insert member is attached to the handle is different from the amount of the notch exposable from the cannula when the second insert member is attached to the handle. In particular cases, the length of the shaft of the insert member is at least approximately the difference between the first length of exposable notch and the second length. The insert member may have a central bar substantially perpendicular to the shaft to which the shaft is attached, and a pair of arms extending from the bar each having a respective tab. In particular embodiments, the shaft has a front surface and at least one lateral camming surface. The camming surface has a slope relative to the front surface and to the direction of travel of the stylet and/or cannula. The handle may include a carriage connected to the outer cannula and adapted to travel in a channel in the handle.

The carriage has a longitudinal groove in some embodiments, so that when the insert member is attached to the handle, the carriage can move with respect to the insert member with its shaft at least partially within the groove. The handle may also include an actuator adapted to be pulled proximally to cock the needle and to be pushed distally to place the stylet and cannula into the noted second relative position. When the insert member is attached to the handle and the stylet and cannula are in that second relative position, the actuator engages the insert member in some embodiments.

There is also disclosed a biopsy needle system having a biopsy needle with a handle, an inner stylet having a notch, and an outer cannula. The handle has a carriage connected to the outer cannula and an actuator connected to the stylet, with the carriage having a longitudinal groove, and the handle has a pair of finger holds. An insert member is provided, adapted for attachment to the handle. Embodiments of the insert member may have a pair of lateral arms and a shaft between the arms. When the insert member is attached to the handle, its shaft is aligned with the groove of the carriage so that the carriage can move with respect to the insert member with its shaft occupying a portion of the groove. The arms of the insert member are inserted through the handle's finger holds so that respective portions of the handle are between the shaft and respective arms. When the insert member is not inserted in the handle, the needle has a default length of the notch that is extended from the cannula during use. When the insert member is inserted in the handle, the needle has a second length of the notch that is extended from the cannula during use, and the second length is less than the default length. A plurality of such insert members can be provided, and in such cases a first insert member may have a shaft of a first length and a second insert member may have a shaft of a second length different from that first length. The insert member(s) may include at least one camming surface on the shaft.

DESCRIPTION OF THE ILLUSTRATED EMBODIMENTS

Figure 1:
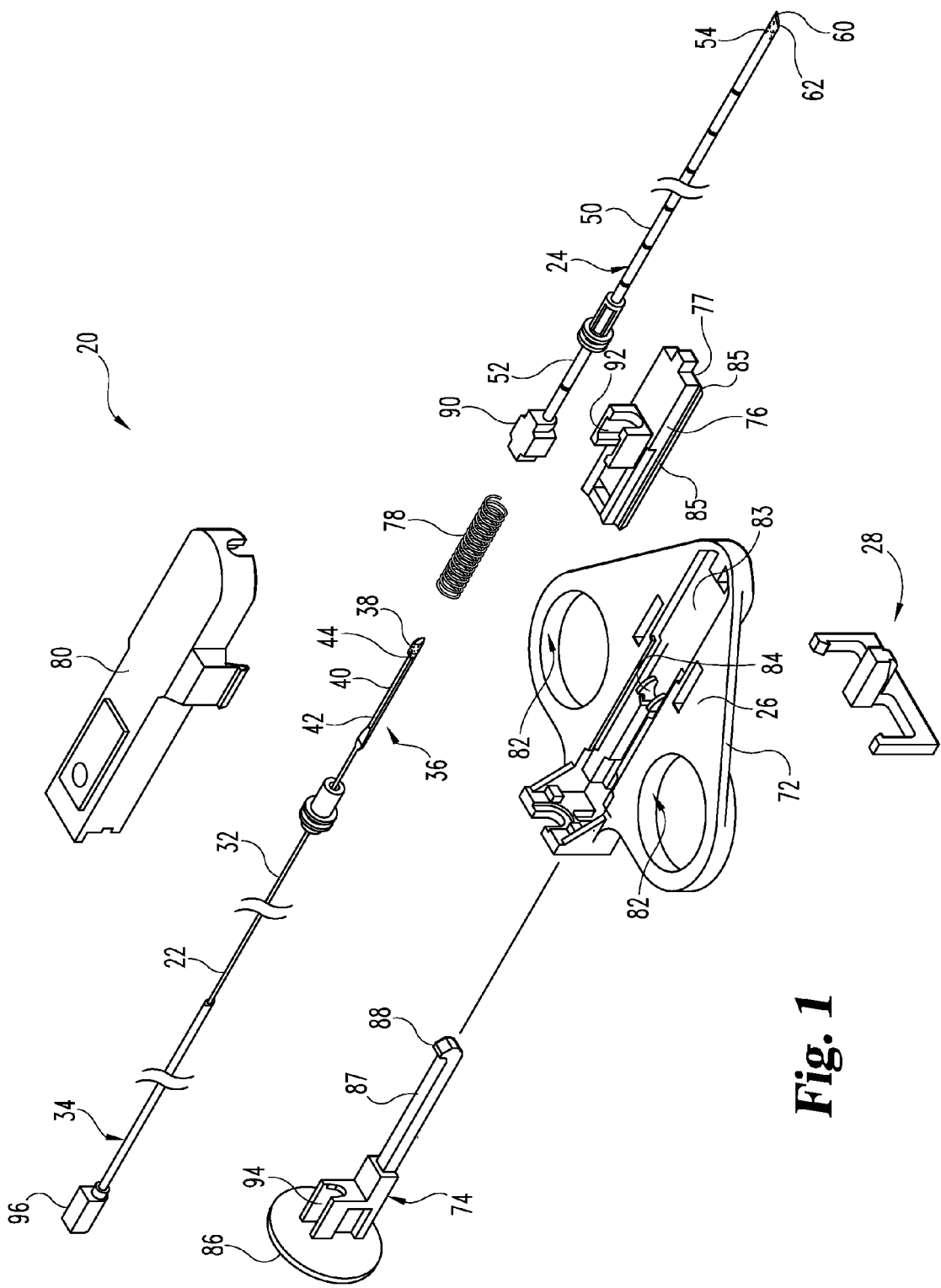
FIG. 1 is an exploded perspective view of an embodiment of a biopsy needle system according to the present disclosure.
Figure 2C:
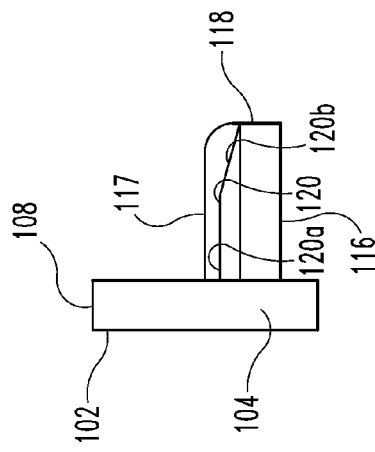
FIG. 2C is a side elevational view of the embodiment of an insert member shown in FIG. 2A.
Figure 2A:
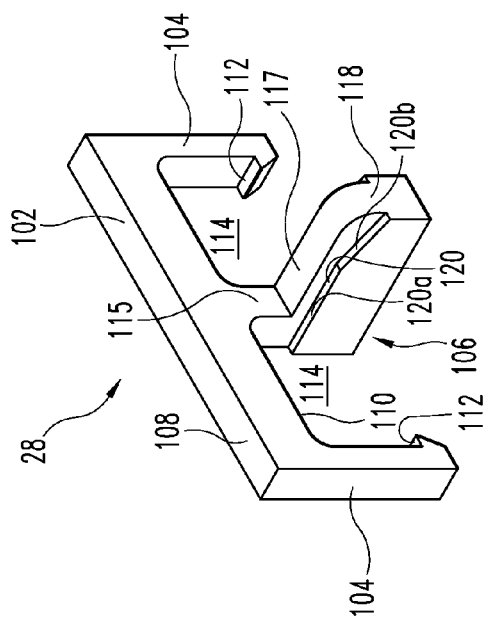
FIG. 2A is a perspective view of an insert member indicated in the embodiment of FIG. 1.
Figure 2B:
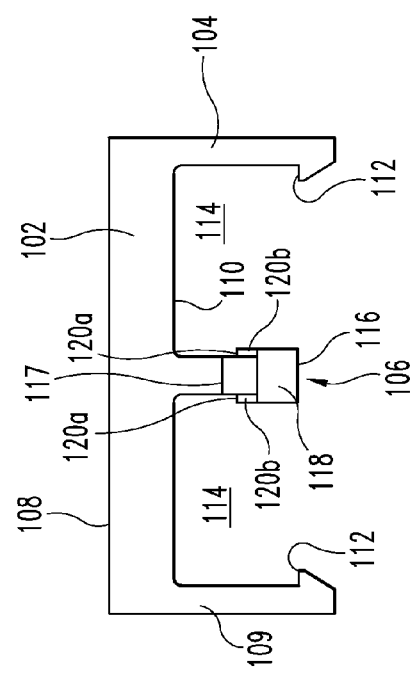
FIG. 2B is a front elevational view of the embodiment of an insert member shown in FIG. 2A.
Figure 3A:
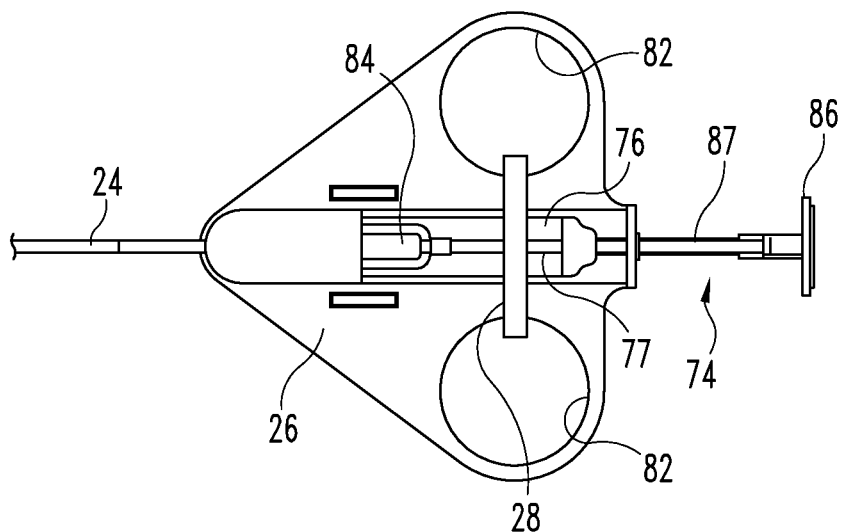
FIG. 3A is a bottom plan view of the embodiment of FIG. 1 in a cocked state.
Figure 3B:
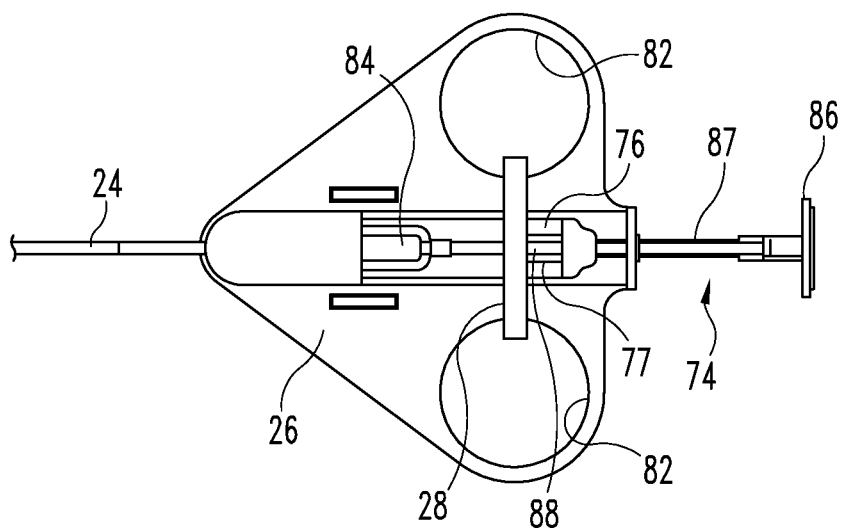
FIG. 3B is a bottom plan view of the embodiment of FIG. 1 in a primed state.

For the purposes of promoting an understanding of the principles of the disclosure, reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates. In several figures, where there are the same or similar elements, those elements are designated with the same or similar reference numerals.

Referring now generally to the drawings, there is shown an embodiment of a biopsy needle system 10, featuring a needle 20. Needle 20 includes an inner member or stylet 22, an outer cannula 24 and a handle 26. Stylet 22 is slidable within cannula 24, and both are connected to and operable by handle 26 in this embodiment. Insert member 28 is provided as a part of system 10, e.g. in a kit, and may be attached to handle 26 to change the sample size obtainable by needle 20, as will be further explained below.

Stylet 22 is substantially cylindrical in the illustrated embodiment, having an elongated body 32 extending between an proximal end 34 and a distal end 36. Elongated body 32 is at least substantially circular in the illustrated embodiment for ease of use and manufacture. Proximal end 34 is connected directly or indirectly to handle 26, for operation during a biopsy procedure as will be further discussed below. Distal end 36 may be sharpened, for example by grinding a surface 38 that is planar and oblique to the longitudinal axis of cannula 22.

Proximal of surface 38 there is formed in stylet 22 a notch or indent 40. In the illustrated embodiment, notch 40 has a depth to a substantially flat inner surface 42 of approximately half of the diameter of stylet 22 or less, and an end surface 44 perpendicular to or forming an obtuse angle with surface 42. It will be understood that other embodiments of notch 40 can be of greater or lesser depths and/or can have end surface 44 oriented with an acute angle between surfaces 44 and 42. In some embodiments, a proximal second end surface 44 may be provided so that notch 40 is bounded both proximally and distally. The illustrated embodiment does not include such a proximal end surface, and so can be used in many needles for various sample sizes. Notch 40 is provided so that tissue to be biopsied enters notch 40, adjacent or against surface 42, and is cut off and contained in notch 40, as further discussed below. As a particular example, notch 40 has a length measured in a proximal direction from end surface 44 of at least 20 mm, so that a default or maximum throw-length for needle 20 is at least 20 mm.

Figure 4A:
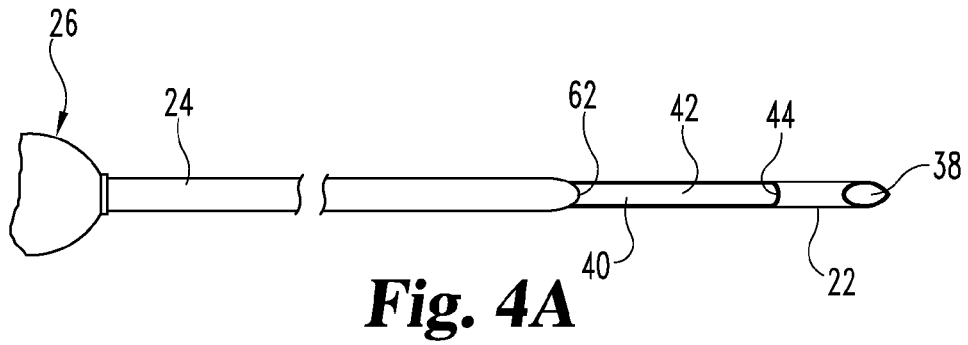
FIG. 4A is a top view of a portion of the embodiment of FIG. 1 in a primed state without an insert member.
Figure 4B:
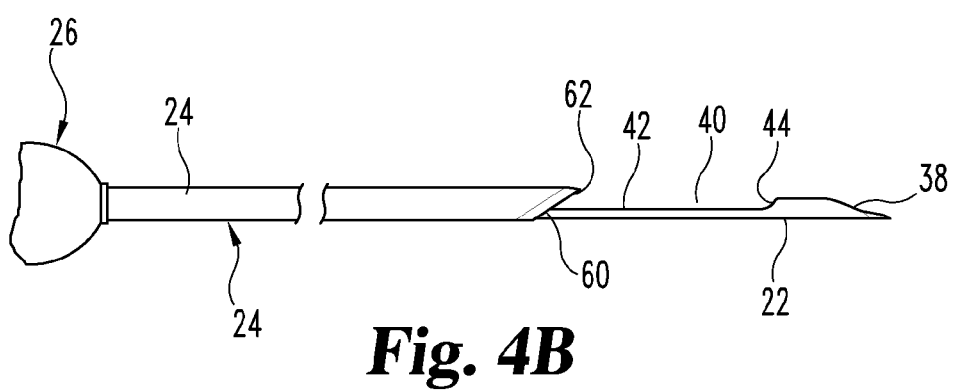
FIG. 4B is a side view of a portion of the embodiment of FIG. 1 in a primed state without an insert member.
Figure 5A:
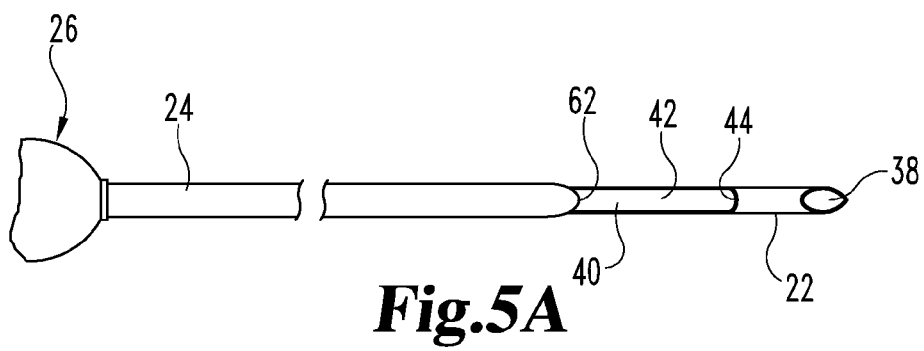
FIG. 5A is a top view of a portion of the embodiment of FIG. 1 in a primed state with an insert member.
Figure 5B:
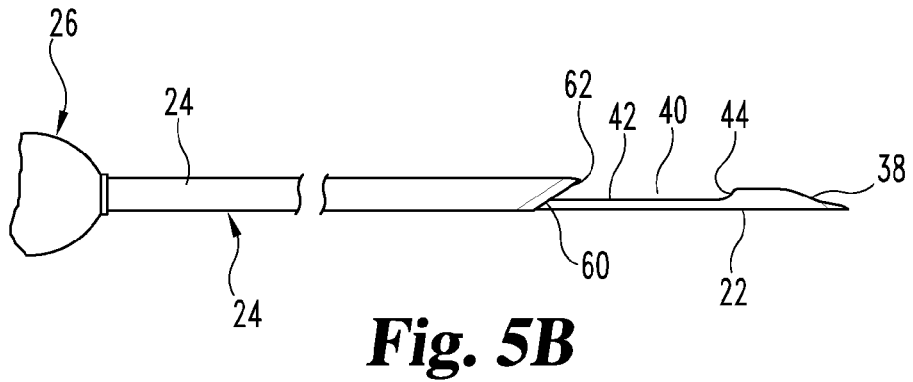
FIG. 5B is a side view of a portion of the embodiment of FIG. 1 in a primed state with an insert member.

The illustrated embodiment of cannula 24 is tubular, having an elongated body 50 extending between a proximal end 52 and a distal end 54. Elongated body 50 is at least substantially circular in the illustrated embodiment, having a cylindrical outer surface 55 and an inner cylindrical surface defining a central lumen, for ease of use and manufacture. Proximal end 52 is directly or indirectly connected to handle 26 for operation during the biopsy procedure. Tubular body 50 is cut obliquely at distal end 54 to form a surface 60 with one or more sharp edges 62. In the illustrated embodiment, an essentially planar oblique section is taken through cannula 24, so that end surface 60 and edge(s) 62 are formed. In the illustrated embodiment, the cut distal end 54 is beveled or otherwise shaped to an edge 62 so as to cut tissue as cannula 24 is advanced. In the illustrated embodiment, surface 60 is formed so that the relatively uppermost portion of cannula 24 (e.g. FIGS. 4B, 5B and as generally inserted into the patient) is distal-most.

Handle 26 is connected to and operates each of stylet 22 and cannula 24 so that stylet 22 is within cannula 24, and so that stylet 22 and cannula 24 are slidable with respect to each other. An example of structure usable as part of handle 26 is that currently used with QUICK-CORE® products sold by Cook Medical (Bloomington, Ind.). Embodiments of structure suitable for use in handle 26 are shown in U.S. Provisional Application No. 61/261,857, filed on Nov. 17, 2009, the entirety of which is incorporated herein by reference.

Handle 26, in the illustrated embodiment, includes a housing 72, trigger or actuator 74, drive carriage 76, spring 78, and cover 80. Housing 72 includes finger holds 82 which are substantially circular in this embodiment, and a central channel 83 in which carriage 76 is slidable forward and backward (proximally and distally). A catch 84 is positioned in channel 83 for holding carriage 76 when carriage 76 is pulled sufficiently proximally, and carriage 76 includes a forward pawl surface 85 (e.g. a rounded edge) on an underside to interact with catch 84. The underside of carriage 76 also includes a longitudinal groove or trough 77. Actuator 74 includes a grip or pad 86 positioned at its proximal end in this embodiment, and a distally-extending finger 87 with an end boss 88 that can engage carriage 76 to draw it proximally. Carriage 76 is coupled to a proximal portion of cannula 24, e.g. by inserting a hub 90 or other portion of cannula 24 into an opening 92 (which may be complementary to hub 90 or other portion of cannula 24) of carriage 76, with cannula 24 extending from carriage 76. In this embodiment, an opening 94 in the structure of actuator 74 is sized and configured to accommodate a portion of hub 96 of stylet 22. Spring 78 is provided adjacent to carriage 76 to propel carriage 76 and cannula 24 forward, as discussed further below. Spring 78 engages carriage 76 and an internal surface of housing 26. Cover 80 fits onto housing 72, covering and protecting spring 78 and sliding engagement between drive carriage 76 and housing 72 from debris and interference.

Insert 28 can be assembled to housing 72 of handle 26 to reduce the travel of stylet 22 and consequently the throw-length of cannula 24 and the ultimate length of sample obtained. In so doing, insert 28 makes the amount of tissue obtainable by needle 20 smaller. As will be discussed further below, use of needle 20 with insert 28 thus results in a smaller length of tissue sample, while use of needle 20 without insert 28 results in a larger sample length.

Insert 28 is generally in the form of a bracket in the illustrated embodiment, having a main bar 102 from which two lateral arms 104 and a central (longitudinal) shaft 106 extend. Bar 102 is linear in this embodiment, having an exterior side 108 and an interior side 110. Bar 102 is a rectangular solid in this embodiment, to maintain a low profile to handle 26 with sturdy support for arms 104 and shaft 106. Lateral arms 104 join and extend away from interior side 110 in a direction perpendicular to side 110. Each arm 104 includes a tab 112, at the end of the respective arms 104 in the illustrated embodiment. Tabs 112 face inward, i.e. toward each other and toward central shaft 106. Tabs 112 form with interior side 110 of bar 102 spaces 114 to either side of shaft 106 in which portions of housing 26 fit, as will be explained below.

Central shaft 106 extends down from at or about the center of bar 102, and also extends away from bar 102 in a direction at least approximately perpendicular to bar 102. Shaft 106 may be considered longitudinally oriented in the main, as it includes or connects to a neck 115 adjoining side 110 and extends along the longitudinal axis of needle 20 when insert 28 is attached to needle 20. Shaft 106 includes a surface 116 that is planar and within the ends of arms 104, or approximately even with surfaces of tabs 112 facing surface 110. An opposing surface 117 is substantially parallel to and between surfaces 116 and 108. Surface 117 curves into a front surface 118 that forms a corner with surface 116 in this embodiment, with surface 118 being perpendicular to surfaces 116 and 117. To either side of surface 117 are lateral edge surfaces 120, each having a portion 120a that is at least substantially parallel to surfaces 117 and 116, and a portion 120b distal from bar 102 that slopes downward from portion 120a toward front surface 118, terminating with or at front surface 118. The length of portion 120b in a particular embodiment is less than that of portion 120a, and may be less than half of the total length of shaft 106. The width of surface 117 is approximately the same as neck 115 extending from surface 110.

The dimensions of insert 28 are determined so as to permit insert 28 to attach tightly and to fit snugly to housing 26, and to block forward movement beyond a predetermined extent of actuator 74 and stylet 22 while allowing insert 28 to transmit force from actuator 74 to carriage 76 and/or catch 84 in handle 26. Accordingly, in the illustrated embodiment the separation between arms 104 and the extension distance of tabs 112 is selected so that arms 104 and tabs 112 fit over one or more portions of housing 26 to form a frictional or interference fit. The length of shaft 106 is or is related to a reduction in sample size realized by using insert 28. In the illustrated embodiment of needle 20, which has an initial or default sample size (e.g. 20 millimeters), the use of insert 28 reduces that default length by the length of shaft 106. A particular length of shaft 106 has a length of 10 millimeters. That is, if needle 20 has a default sample length of 20 millimeters and shaft 106 has a length of 10 millimeters, then the sample length for that needle with insert 28 fitted to it is the difference of 10 millimeters.

Insert 28 is shown as a unitary or monolithic piece in the illustrated embodiment, so that shaft 106 is fixed to neck 115 and bar 102. It is contemplated that in other embodiments shaft 106 may be movable along its longitudinal axis (i.e. generally perpendicular to bar 102) relative to bar 102 and/or neck 115. When insert 28 is attached to handle 26 (further described below), shaft 106 would be movable along and relative to channel 77 of carriage 76. In such embodiments, movement of shaft 106 may allow for easier insertion in and attachment to handle 26, and for maintaining shaft 106 out of contact with carriage 76 and/or catch 84 until a priming step for needle 20 (described below).

A kit or system 10 includes a needle 20 and one or more inserts 28. The clinician can use the needle without any insert 28 to obtain a sample of the default sample size (or throw-length) of the needle. If the clinician determines that a smaller size of sample is necessary or desirable, he or she can fit an insert 28 to housing 26 as described herein and use the modified needle to obtain the smaller sample. If multiple inserts 28 are provided in such a kit or system, respective inserts 28 may have different lengths of shaft 106 so that the clinician can choose the particular insert 28 to use with the needle to provide a sample size of or closer to the desired sample size. Such additional inserts 28 provide additional choices and flexibility to the clinician to obtain the sample size that the particular patient needs, and the decision on sample size can be made or determined at the time of the sample without preparation of multiple needles or other substantial structure.

Handle 26 is cocked by pulling actuator 74 (e.g. via grip 86) backward, i.e. out or away from housing 72. With boss 88 of actuator 74 engaging carriage 76, when actuator 74 is pulled out from housing 72, carriage 76 is pulled backward (proximally) within channel 83, compressing spring 78 between wall 28 and carriage 76. Catch 84 engages the underside of carriage 76 (e.g. pawl surface 85) to maintain a cocked position. Pulling grip 86 proximally moves both cannula 24 and stylet 22 together, maintaining their respective tips at approximately the same location.

Once needle 20 is cocked, the user pushes grip 86 to move actuator 74 forward a distance sufficient to prime needle 20 by moving notch 40 of stylet 22 out of the distal end of cannula 24 (e.g. FIGS. 4A-5B). Such forward movement of actuator 74 moves stylet 22 because of the connection of stylet 22 with actuator 74, but does not move carriage 76 and cannula 24 because bos 88 does not push carriage 76. When notch 40 is exposed, further forward movement of actuator 74 (and stylet 22) is impeded by carriage 76 and/or catch 84. As will be explained further below, this priming step is performed once needle 20 is inserted into the patient so that the distal ends of stylet 22 and cannula 24 are in or almost in the tissue to be sampled, and operates to allow tissue into notch 40.

In situations in which insert 28 is not used, this priming step operates to expose notch 40 to the maximum or default extent. That is, stylet 22 is extended so that the maximum or default length of tissue can enter into notch 40. Use of insert 28 limits the distance stylet 22 can be moved forward in the priming step. Shaft 106 blocks the path of finger 87 and boss 88 of actuator 74, allowing them to travel forward in a priming step until boss 88 contacts insert 28, or until actuator 74 moves shaft 106 into contact with a portion of carriage 76 and/or catch 84. For example, the rearward- or proximal-most part of shaft 106 provides the surface that contacts finger 87 and/or boss 88 and indicates to the user that the priming step has been accomplished and no further pushing on actuator 74 should be done until firing of needle 20 is desired. If insert 28 is not present, carriage 76 blocks the path of finger 87 and/or boss 88 in the priming step.

Needle 20 is fired to capture tissue within notch 40 by releasing spring 78 to move cannula 24 quickly forward. From the primed state, pushing grip 86 further toward housing 26 results in a force applied (through actuator 74) to carriage 76 and/or catch 84, e.g. finger 87 and/or boss 88 lifting or pushing carriage 76 and/or pivoting catch 84, so as to release the hold on spring 78 and allow its stored energy to be used to push drive carriage 76 and thrust cannula 24 over notch 40 of stylet 22. In situations in which insert 28 is attached to housing 26, pushing grip 86 toward housing 26 from the primed configuration presses boss 88 against insert 28. Shaft 106 is pushed forward, with its end shaped similarly to that of boss 88 in this embodiment, resulting in the release of carriage 76 and forward propulsion of cannula 24. For example, sloped camming surfaces 120b may engage a portion of catch 84 or carriage 76 to pull catch 84 away from carriage 76 or lift carriage 76 away from catch 84. Conversely, if insert 28 is not present, pushing grip 89 forces boss 88 directly against carriage 76 and/or catch 84 to allow carriage 76 and cannula 24 to shoot forward.

Thus, in the illustrated embodiment firing the cocked, inserted and primed needle 20 propels cannula 24 over stylet 22, and particularly over notch 40 or the portion of notch 40 that extends from the distal end of cannula 24. The cutting action of cannula 24 via its sharpened edge(s) 62 during that movement severs and traps tissue within notch 40. The illustrated embodiment of needle 20 is accordingly a single action biopsy device effective to obtain two or more sizes of tissue sample.

Handle 26 permits a cocking step that prepares the handle to fire cannula 24 over and along stylet 22, an insertion step in which the relatively positioned stylet 22 and cannula 24 are inserted into the body, and a firing step in which cannula 24 is released to move forward rapidly (pushed forward by spring 78) over stylet 22 and return to or toward the unstressed state. The cocking step is performed by holding finger holds 82 and pulling back on actuator 74 until carriage 76 and catch 84 click as discussed above. Inserting needle 20 is accomplished while holding finger holds 82 by forcing handle 26 (and connected stylet 22 and cannula 24) forward into the body. If the cocking step precedes the insertion into the body, then handle 26 should be pushed forward during the insertion step without pushing on actuator 74. Pushing actuator 74 forward gently following insertion moves notch 40 out from cannula 24, and allows tissue into notch 40. Firing cannula 24 is accomplished by pushing forward actuator 74 to overcome the cocked state, and may be accomplished by the same hand that holds finger grips 82 in this embodiment. The firing propels cannula 24 over stylet 22 and through tissue, trapping a length of tissue in notch 40. The steps noted above may be applied in a different order, as may be indicated by the clinical situation or the particular operating mode(s) of needle 20.

If insert 28 is to be used to change the default sample size obtained by needle 20 to another size, it may be inserted into handle 26 following the cocking step in a particular embodiment so as not to interfere with the movement of parts during cocking. In the illustrated embodiment, cocking handle 26 exposes at least a portion of groove 77 in carriage 76 as seen from the underside of handle 26 (i.e. the side opposite cover 80). Insert 28 is inserted into handle 26 so that shaft 106 enters groove 77 in an angled orientation (i.e. non-parallel to groove 77 or channel 83, with front surface 118 inserted first) and is rotated into place. By inserting front surface 118 first, and rotating or pivoting the rest of shaft 106 into groove 77, pressure by shaft 106 against carriage 76 or catch 84 is reduced or eliminated. The user can also hold or place backward (distal) pressure on actuator 74 to counteract any forward pressure placed on carriage 76 or catch 84 during insertion of shaft 106. As insert 28 is pivoted into place, arms 104 go through respective finger holds 82 so that tabs 112 snap on and lie on the top side of handle 26 lateral of cover 80. Thus, portions of housing 72 fit in spaces 114 between arms 104 and shaft 106 of insert 28 with a snap or interference fit. As arms 104 go through finger holds 82, remaining parts of shaft 106 of insert 28 enter groove 77 of carriage 76 within channel 83, so that shaft 106 is maintained at least partially within groove 77 along the entire length of shaft 106. Shaft 106 is thus positioned so that it is aligned linearly with groove 77 and carriage 76, and in this embodiment extends toward (and in particular embodiments engaging or in close apposition to) carriage 76 and/or catch 84. Thus, if insert 28 is used, shaft 106 is held distal of finger 87 and boss 88. Instead of finger 87 and boss 88 directly contacting carriage 76 and/or catch 84 in priming or firing needle 20, finger 87 and boss 88 will contact shaft 106, which transmits the force to fire carriage 76 forward. Once fired, carriage 76 will travel forward (distally) until it contacts insert 28, e.g. a portion of shaft 106, neck 115 and/or bar 102.

Cannula 24 and stylet 22 are slidable with respect to each other, as indicated above. Stylet 22 extends from its connection with handle 26 through the lumen of outer cannula 24. In a particular embodiment, the outer diameter of inner member 22 is approximately the same as the inner diameter of outer cannula 24, so that there is little play of space between cannulas 22 and 24, yet they can move smoothly with respect to each other. Stylet 22 and cannula 24 have a first relative position which is seen before cocking or after firing needle 20. In that first relative position, stylet 22 and cannula 24 are approximately coextensive in the illustrated embodiment, i.e. distal ends of stylet 22 and cannula 24 are at approximately the same location. A second relative position between stylet 22 and cannula 24 has stylet 22 extending from cannula 24 so that at least a portion of notch 40 is exposed.

The use of needle 20 will now be described in the context of obtaining a sample of soft tissue for testing purposes. It will be understood that methods for obtaining samples of other tissues or for other purposes are also contemplated.

The surgeon or other medical professional first determines a location in a patient, with its depth under the skin, from which a tissue sample is desired. In one embodiment, stylet 22 and cannula 24 of needle 20 are initially in the above-noted first relative position, e.g. with the distal ends of stylet 22 and cannula 24 co-extant or adjacent. The user considers what length of sample he or she believes is needed. The illustrated embodiment provides a choice between two throw lengths, e.g. 10 millimeters (with an embodiment of insert 28 in fitted onto handle 26) and 20 millimeters (a default size, without an insert 28 attached). If the user desires a 20 millimeter sample, he or she does not attach insert 28 to handle 26 and proceeds to use needle 20 as indicated. If the user desires a 10 millimeter sample, he or she fits insert 28 into handle 26, and proceeds to use needle 20.

In either usage, the user must pull actuator 74 the same distance to cock needle 20. The user cocks needle 20, as noted above, by pulling actuator 74 of handle 26 until carriage 76 catches on catch 84. In the cocked state, in this embodiment, stylet 22 and cannula 24 are in a relative position with ends of stylet 22 and cannula 24 substantially coinciding. If insert 28 is to be used, it is inserted (as indicated in the above embodiment) following cocking of needle 20, and its distal end 118 abuts or is closely adjacent to an end of carriage 76 and/or catch 84 following insertion. If insert 28 is not used, carriage 76 does not abut anything at its distal end, until finger 87 and/or boss 88 is adjacent or abuts it when needle 20 is primed.

In that state, the user places distal ends 36 and/or 54 of stylet 22 and/or cannula 24 against the skin at a place proximate to the desired location, and inserts needle 20. Needle 20 forces a path through the skin and subcutaneous tissue to a point in or just before the location from which a sample is to be taken. The path size and shape is determined by the outer configuration of cannula 24. In embodiments in which cannula 24 is very thin, the path is not substantially larger than the outer diameter of stylet 22, reducing discomfort from the biopsy procedure.

Actuator 74 is then moved forward an amount permitted by handle 26 until further movement is obstructed, e.g. by insert 28, if present, or by carriage 76 and/or catch 84 if not. That advancement moves notch 40 beyond cannula 24 (e.g. FIGS. 4A-5B), as noted above, to face or be adjacent to tissue to be sampled. With insert 28 in place in housing 26, actuator 74 is only advancable to a point where boss 88 contacts insert 28, which is less than the default advancement possible when insert 28 is absent. In the particular example noted above, without insert 28, actuator 74 is advanceable through a length of approximately 20 millimeters, resulting in approximately 20 millimeters of exposure of notch 40 from the distal end of cannula 24 and into tissue to be sampled. With insert 28 attached to handle 26 as discussed, actuator 74 is advanceable through a length of only about 10 millimeters (i.e. the default length less the length of shaft 106), resulting in approximately 10 millimeters of exposure of notch 40 from the distal end of cannula 24 and into tissue.

When stylet 22 is advanced to the extent permitted, and with tissue in the exposed portion of notch 40, the user fires cannula 24 forward by pressing actuator 74. Spring 78 releases its energy (from the cocking step) to push carriage 76 forward (distally), propelling cannula 24 over stylet 22 and through the tissue. With insert 28 attached to handle 26 as discussed, carriage 76 is pushed forward until it is blocked by insert 28. Thus, carriage 76 (with cannula 24) is propelled forward by approximately the distance that stylet 22 was extended from cannula 24 in the priming step. If insert 28 is not used, carriage 76 and cannula 24 travel distally in the firing step to the maximum extent permitted by channel 83 in handle 26. The cutting action of cannula 24 severs the sample of tissue within notch 40. Tissue outside notch 40, either radially or longitudinally, is not trapped in notch 40 between cannula 24 and stylet 22. Cannula 24 and stylet 22 may return to a position with their respective ends at or adjacent to each other.

After firing, needle 20 is withdrawn from the patient. Once needle 20 is withdrawn, the tissue sample is removed by cocking and priming needle 20, as indicated above, to expose notch 40 and the tissue within it. If insert 28 was used during the acquisition of tissue, it may be removed from handle 26 prior to unloading if desired. Removing insert 28 prior to unloading permits notch 40 to be exposed to the fullest or default extent during unloading, thus providing space around the sample to ease removal of it from notch 40. The tissue sample can be extracted from notch 40 using a forceps or other tool, or in some embodiments by inverting notch 40 and allowing the tissue to drop out of notch 40 into a specimen dish or other container. If the user determines that additional sample(s) are needed, then the procedure above can be repeated to obtain such samples.

In particular, it is noted that there may be occasions in which the user chooses a throw-length for needle 20, uses needle 20 without insert 28 to obtain a sample, and then determines that the obtained sample is too long (e.g. it obtains all or a significant amount of tissue not of interest to the clinician). In such cases, the user can re-use needle 20 with insert 28 fitted with insert 28 as discussed previously, repeating the sampling process to obtain a new sample of the new size. Similarly, if a user obtains a sample that is too small using needle 20 that has an insert 28 attached, the user can re-use needle 20 with the insert 28 removed to obtain a new sample of a larger length.

The illustrated embodiment of system 10 has two throw-length settings, exemplified as 10 millimeters (with insert 28 attached) and 20 millimeters (the default condition, without insert 28 attached). It will be understood that other default throw lengths and/or other length adjustments via an insert member can be used in place of one or both of such lengths. Further, as noted previously it will be understood that three or more throw-length settings may be provided in a needle system or kit, by providing two or more inserts 28 each having respective different lengths of shaft 106, in addition to the default throw-length. As one example, a system or kit may be provided having sterilized parts including a needle 20 with a default throw-length of 20 millimeters, and two inserts 28, the longitudinal shaft 106 of one having a length of 5 millimeters and that of the other having a length of 10 millimeters. That kit can be used as the clinician needs, to provide a biopsy sample having a length of 20 millimeters (using neither insert), of 15 millimeters (using the insert having a shaft-length of 5 millimeters), or of 10 millimeters (using the insert having a shaft-length of 10 millimeters).

As used herein, the term "throw length" is intended to indicate a measurement of the length of a tissue sample obtained and/or the distance a part is moved forward in use of the device. For example, a 20 millimeter throw length for the embodiments noted above indicates that stylet 22 is advanced in the priming step so that approximately 20 millimeters of notch 40 (or the entire notch 40 if its length is 20 millimeters, in this example) is exposed from cannula 24.

In the illustrated embodiment, stylet 22 has a close fit with cannula 24 within its lumen 58, and the two are slidable with respect to each other. By having both a "close fit" and slidability, it is meant that there is no substantial separation or gap between stylet 22 and cannula 24, as by a boss or flange. As seen in the embodiments in the drawings, stylet 22 and cannula 24 have a close and slidable fit at least along their respective distal ends, and in some embodiments that close and slidable fit extends along all or substantially all of one or both of their respective lengths. Such a configuration minimizes the external size of a needle needed to obtain a particular amount of tissue.

Such tissue sampling devices reduce the inventory that must be kept by hospitals, clinics or other medical-care facilities, freeing shelf space available to clinicians. Currently, a clinician needs multiple editions of each biopsy device (e.g. a 10 mm version, a 20 mm version, and perhaps others) for each gage of stylet and cannula combination, and for each patient. Combining multiple settings into one system or kit will cut the product shelf volume, and the number of products to be available for each patient, to a fraction of what is currently needed.

While the disclosure has been illustrated and described in detail in the drawings and foregoing description, the same is to be considered as illustrative and not restrictive in character, it being understood that only certain specific embodiments have been shown and that all changes and modifications that come within the spirit of the disclosure are desired to be protected. It is to be understood that features described with respect to one embodiment or aspect of the disclosure can be used with other embodiments or aspects of the disclosure.

What is claimed is:

1. A biopsy needle, comprising:
   an inner stylet member having a distal end and defining a longitudinal notch of at least a default length;
   an outer cannula member having a sharpened distal end and a lumen, said stylet member being slidable in said lumen;
   a handle connected to each of said stylet member and said cannula member, said handle being operable to move said stylet member and said cannula member with respect to each other;
   an insert member separate from and attachable to said handle, wherein when said insert member is not attached to said handle, said needle has a first sampling size, and when said insert member is attached to said handle, said needle has a second sampling size less than said first sampling size; and
   wherein said handle includes a pair of finger holds, and said insert member includes a pair of arms laterally offset from a central shaft, and each of said arms connects to said handle at a respective one of said finger holds.

2. The biopsy needle of claim 1, wherein said first sampling size is equal to or less than said default length of said notch.

3. The biopsy needle of claim 1, wherein said central shaft includes at least one longitudinally-oriented camming surfaces.

4. The biopsy needle of claim 1, wherein said handle includes a central longitudinal channel, and said central shaft occupies a portion of said channel.

5. The biopsy needle of claim 1, wherein said inner stylet is adapted to extend from said cannula, and wherein the maximum amount of said stylet that can extend from said cannula is greater when said insert member is not attached to said handle than when said insert member is attached to said handle.

6. The biopsy needle of claim 1, wherein said handle includes a carriage having a longitudinal groove and being connected to said cannula member, and wherein when said insert member is attached to said handle, at least a portion of said insert member is linearly aligned with said groove.

7. The biopsy needle of claim 1, wherein a plurality of insert members are provided, each said insert member having a respective shaft, and wherein each said shaft has a different length.

8. The biopsy needle of claim 1, wherein when said insert member is attached to said handle member, said central shaft impedes distal movement of said stylet relative to said cannula.

9. A biopsy system, comprising:
   a biopsy needle having a handle, an outer cannula, and an inner stylet having a longitudinal notch, said stylet and said cannula being movable with respect to each other between a first relative position in which said notch is within said cannula and a second relative position in which at least a portion of said notch is exposed from said cannula; and
   at least one insert member having a central shaft and adapted to be attached to said handle,
   wherein said biopsy needle has a default condition in which the amount of said notch exposable from said cannula has a first length, and when one of said at least one insert member is attached to said handle, the amount of said notch exposable from said cannula has a second length less than said first length, and wherein said handle includes a carriage connected to said outer cannula, said carriage adapted to travel in a channel in said handle, said carriage having a longitudinal groove, and wherein when said insert member is attached to said handle, said carriage can move with respect to said insert member with said shaft of said insert member at least partially within said groove.

10. The system of claim 9, wherein at least two said insert members are provided, and wherein the shaft of a first said insert member has a first length, and the shaft of a second said insert member has a second length different from said first length, so that the amount of said notch exposable from said cannula when said first said insert member is attached to said handle is different from the amount of said notch exposable from said cannula when said second insert member is attached to said handle.

11. The system of claim 9, wherein said shaft has a length, and said length of said shaft is at least approximately the difference between said first length and said second length.

12. The system of claim 9, wherein said insert member has a central bar substantially perpendicular to said shaft to which said shaft is attached, and a pair of arms extending from said bar, each of said arms having a respective tab.

13. The system of claim 9, wherein said shaft of said insert member has a front surface and at least one lateral camming surface, said camming surface having a slope relative to said front surface and to said direction of travel.

14. The system of claim 9, wherein said handle includes an actuator adapted to be pulled proximally to cock said needle and to be pushed distally to place said stylet and cannula into said second relative position, and wherein when said insert member is attached to said handle and said stylet and cannula are in said second relative position said actuator engages said insert member.

15. A biopsy needle system comprising:
   a biopsy needle having a handle, an inner stylet having a notch and an outer cannula, said handle having a carriage connected to said outer cannula and an actuator connected to said stylet, said carriage having a longitudinal groove, and said handle having a pair of finger holds; and an insert member adapted for attachment to said handle, said insert member having a pair of lateral arms and a shaft between said arms, wherein when said insert member is attached to said handle said shaft is aligned with said groove of said carriage so that said carriage can move with respect to said insert member with said shaft occupying a portion of said groove, and said arms are inserted through said finger holds so that respective portions of said handle are between said shaft and respective said arms, and wherein when said insert member is not inserted in said handle, said needle has a default length of said notch that is extended from said cannula during use, and when said insert member is inserted in said handle, said needle has a second length of said notch that is extended from said cannula during use, and said second length is less than said default length.

16. The system of claim 15, wherein a plurality of said insert member is provided, and wherein a first of said insert member has a shaft of a first length, and a second of said insert member has a shaft of a second length different from said first length.

17. The system of claim 15, wherein said insert member includes at least one camming surface on said shaft.

18. A biopsy needle, comprising:

an inner stylet member having a distal end and defining a longitudinal notch of at least a default length;

an outer cannula member having a sharpened distal end and a lumen, said stylet member being slidable in said lumen;

a handle connected to each of said stylet member and said cannula member, said handle being operable to move said stylet member and said cannula member with respect to each other;

an insert member separate from and attachable to said handle, wherein when said insert member is not attached to said handle, said needle has a first sampling size, and when said insert member is attached to said handle, said needle has a second sampling size less than said first sampling size;

wherein said handle includes an actuator adapted to be pulled proximally to cock said needle; and wherein said needle is configured to allow attaching of said insert member when said needle is cocked, and wherein said handle includes a carriage connected to said outer cannula member, said carriage adapted to travel in a channel in said handle, said carriage having a longitudinal groove, and when said insert member is attached to said handle, said carriage can move with respect to said insert member with said shaft of said insert member at least partially within said groove.

19. A biopsy needle, comprising:

an inner stylet member having a distal end and defining a longitudinal notch of at least a default length;

an outer cannula member having a sharpened distal end and a lumen, said stylet member being slidable in said lumen;

a handle connected to each of said stylet member and said cannula member, said handle being operable to move said stylet member and said cannula member with respect to each other;

an insert member separate from and attachable to said handle, wherein when said insert member is not attached to said handle, said needle has a first sampling size, and when said insert member is attached to said handle, said needle has a second sampling size less than said first sampling size;

wherein said handle includes a carriage having a longitudinal groove and being connected to said cannula member, said carriage adapted to travel in a channel in said handle, and wherein when said insert member is attached to said handle, at least a portion of said insert member is linearly aligned with said groove, and said carriage can move with respect to said insert member with said shaft of said insert member at least partially within said groove.

\* \* \* \* \*